US007762257B2

(12) United States Patent
Chiam

(10) Patent No.: US 7,762,257 B2
(45) Date of Patent: Jul. 27, 2010

(54) SECURE NANO-MASK

(75) Inventor: Kia Chee Chiam, Singapore (SG)

(73) Assignee: i-Nano Industries Pte Ltd., Singapore (SG)

( * ) Notice: Subject to any disclaimer, the term of this patent is extended or adjusted under 35 U.S.C. 154(b) by 893 days.

(21) Appl. No.: 11/638,124

(22) Filed: Dec. 13, 2006

(65) Prior Publication Data

US 2007/0267022 A1 Nov. 22, 2007

(30) Foreign Application Priority Data

May 19, 2006 (TW) .............................. 95118019 A

(51) Int. Cl.
*A61M 11/00* (2006.01)

(52) U.S. Cl. ............................ 128/206.21; 128/206.12; 128/206.19

(58) Field of Classification Search ................................ 128/205.27–205.29, 206, 206.12–206.17, 128/206.19, 206.21
See application file for complete search history.

(56) References Cited

U.S. PATENT DOCUMENTS 4,863,779 A * 9/1989 Daponte ..................... 428/152
2004/0078860 A1* 4/2004 Bell et al. .......................... 2/9
2004/0178135 A1* 9/2004 Beplate ................... 210/321.6

* cited by examiner

*Primary Examiner*—Steven O Douglas
(74) *Attorney, Agent, or Firm*—Bucknam and Archer

(57) ABSTRACT

A close-fitting face mask made of woven or non-woven material having a fitted nose area with a nose-bridge contact and a nose-bridge recess or space, a nose upper part extending from the nose-bridge contact at the mid point of the bridge of the wearer's nose to the level of the lower eyelid, a chin part with a recess or space extending below the wearer's chin, and attachment straps made of elastic or flexible material including upper straps, one each side, attached to the nose upper part and passing above the upper part of the wearer's ear, and lower straps, one each side, attached to the pivot or neutral point of the mask and passing below the wearer's ear.

9 Claims, 2 Drawing Sheets

Angle a = 45 deg (30-60 deg)
Angle b = 25 deg (10-40 deg)

Angle a = 45 deg (30-60 deg)
Angle b = 25 deg (10-40 deg)

Angle a = 50 deg (40-70 deg)
Angle b = 40 deg (20-50 deg)

SECURE NANO-MASK

FIELD OF INVENTION

This invention relates to protection against microbial infection or cross contamination of microbes. It is apparel in the form of a face mask worn to provide a primary barrier between the wearer and the environment and vice versa while permitting comfortable breathing. The face mask is effective in three areas firstly being close fitting and secure against moving off the face either upwards or downwards by innovations of design and catchment to he wearers head taking into account the forces applied to the mask by the wearer, secondly by the use of a residual non-volatile, nanotechnological antimicrobial agent, and thirdly by effectively preventing the wearer being exposed to allergens such as spores, pollens and particles thereof.

BACKGROUND OF THE INVENTION

Background Art

In the modern society human to human contact is much more frequent and thus bacterial and viral infections of increasing virulence are on the increase. These infections and their causes are without boundaries of country, race or religion and the risk is global.

A breakthrough of barrier protection is needed with the main criteria being cross-contamination safe, user friendly, allowing comfortable breathing. The nanotechnology protective products exemplified by the Secure-nano Mask have been invented and developed to provide this barrier protection.

There are several problems arising from the approaches currently used by manufacturers of face masks.

These arise either from (1) failure to fit the face (2) failure to secure the mask from moving (3) failure to provide an effective barrier against microbial cross infection to or from the mask (4) failure to provide or the absence of a durable anti-microbial means or mechanism for killing microbes (5) poor efficacy of eliminating other contaminating agents such as spores and pollen or (6) not providing for comfortable breathing.

To overcome all the abovementioned problems the inventors propose innovations that provide a secure-to-wear mask with an effective barrier with lethal effect against microbes as well as protection against particulate matter and potential allergens.

The specifications of these innovations are proposed under four headings:

1. Structural Changes

The innovation in the mask has been made to overcome the disadvantages of the existing masks in the market which while they may look satisfactory they do not function well in certain ways.

The following innovations are disclosed:

1.1 mask profile has extensions to the nose contacting part providing a nose-bridge recess or pocket into which the nose fits comfortably and securely, formed by the shape of the material and the sealed edge applied.

1.2 the mask extends lower and under the chin having a roomier fit to the chin but providing a close fit to the cheeks and lower jaw, thus a chin recess formed by the material of the mask and the sealed edges in manufacture, allowing greater flexibility when the jaw is moved for whatever purpose, such as in talking, yawning or coughing. The greater outer edge contact secures the mask comfortably and maintains a barrier.

2. Fit to Face

The fit to the face is excellent particularly on the nose and cheeks areas with a close fit preventing opening up and thus effectively reducing not only microbial entry or exit on the sides but that of odours, aerosols and or toxic materials. Furthermore the exit of breath is directed downwards significantly reducing fogging of glasses and/or protective goggles. The chin region has been elongated to allow for comfortable chin movement when opening mouth for talking, coughing and yawning.

3. Security when Wearing

The major disadvantage of all other masks examined and tested has been that they fail to secure the masks to the face unless the face of the wearer face is kept still or immobile. The inventors have provided for security or 'hold' to the face when speaking or moving the lower part of the face.

(i) The new mask has a secured nose-bridge recess and extended chin space such that the mask does not slide upwards into the eye area, exposing the mouth and (ii) The new mask does not slide off the face downwards over the chin exposing the nose. Both events remove the anti-microbial barrier to both wearers and other people in their presence.

(iii) The new mask has also unique straps design different to all other masks examined and tested. The main forces applied by the straps are now directed upwards to the ear and backwards to the upper cheek area. These forces balance the mask at the mid point (see diagram) and counter the forces exerted by the chin area when moving the mouth or chin. The resultant forces ensure that the mask remains secure and whether moving upwards or downwards slightly will return to the mid position as established by the user when donning the mask 4. Barrier Effectiveness The inventors note that ordinary mask material only provides filtering but propose that the new mask has advantages of barrier effectiveness combined with microbial killing capability because it:

(i) fits closely on all area of the face with minimal movement away from facial contact when the wearer speaks or opens their mouth for any purpose.

(ii) The mask is impregnated with i-nano material unique to this application that prevents microbial contamination by causing microbe-membrane damage. Microbes coming in contact with the i-Nano mask and thus the nanotechnology material, either outward from the wearer or inward from the external environment, which includes other people, will be attracted by electro-charge attraction effecting membrane damage and rupture and therefore killed. Because the nano-material is residual on the mask the killing effect of the i-nano mask continues for as long as the mask is worn. Over 50 forms of bacteria are killed by the material and the inventor proposes that all membrane-bound organisms are at risk from the nanotechnology killing effects.

Any existing treatments to masks of an anti-microbial nature involve chemicals which may be harmful with extended use or of temporary duration if volatile in nature. The reactions with microbes are largely chemical in nature. The i-nano treated face mask works by physical principles and action whereby the nano material is in the form of nano-needles which attack and rupture any microbial membrane be it from a bacterium, mould, fungus, mycelium, yeast, spore or membrane-bound virus.

(iii) Furthermore any cross contamination from hand to mask or mask to hand will be minimised by the contact of the microbes with the lethal i-nano product that starts the anti-microbial process.

(iv) The i-nano mask has also undergone extensive testing by the University of Singapore and has been conclusively shown to exclude pollen particles from designated trees (Japanese Sugo) and plants. The non-woven mask material was 96% effective at excluding the pollen particles.

DESCRIPTION OF THE DEVICE

The mask is manufactured in two identical upper and lower parts each consisting of (i) A strip of one or more layers to form the mask (ii) A strip of one-way flexible material to form the straps to be worn fixed to the ear, neck or back of head.

(iii) i-nanomaterial impregnated into the non-woven material of the face covering part of the mask.

(iv) Formulated to prevent allergenic agents such as spores and pollens from being ingested by the wearer.

A color or pattern may be applied to the appearance of the mask portion as fashion statement and to remove the impact that the wearer is wearing a protective device.

SUMMARY OF THE INVENTION

In its broadest independent aspect, the invention provides a barrier aid comprising a face mask with fitted nose area, chin space which is attached by straps such that the forces and vectors of those forces exerted by the straps ensure the mask does not ride up or down but remains secure even when facial movement, especially the chin, is moved even to its widest extent and closed again an unlimited number of times a) The nose recess is defined at an angle between 30 and 60 degrees but preferably at 45 degree to the vertical.

b) The nose upper part extends from the mid point of the bridge of the nose to the level of the lower eyelid.

c) The chin space provided is between 10 and 15 mm below the closed-mouth chin level and preferably 12 mm space but fitting underneath and at the sides of the said chin.

d) The two attachment straps made of one-way elastic material are made in such a way as the upper straps, one each side, are attached to the mask points on each side level with the upper part of the mask and in the closed-mouth position are inclined at an angle of between 30 and 60 degrees but preferably at 40 degrees to the horizontal and passes above the upper part of the ear. The lower straps, one each side, are attached to the mid point of the mask, i.e. the balance or pivot point passing between +10 and +40 degrees from the horizontal but preferably 25 degrees to horizontally to under the lower part of ears, one each side. The straps are joined and continuous and loop around the ear, but may be fixed to the wearer around the back of the head at the appropriate level.

In the open mouth or fully extended jaw position the jaw is moved downwards and rearwards such that the angel of the straps is altered and the forces upon them changed to maintain the mask securely on the wearer's face. The upper straps one per side are thus inclined at an angle of between 40 and 70 degrees and preferably at 50 degrees while the lower straps one per side are inclined at 20 to 50 degree and preferably at 40 degrees to the horizontal when the wearer is standing upright.

e) The mask material is special formula impregnated with a solution of nanotechnology antimicrobial particles which is allowed to dry and become residual in the non-woven matrix of the mask material.

Aspect a) of the mask in FIG. 1 is particularly advantageous when the wearers face is in a normal closed mouth position, because the angle of the attachments of the mask to the wearer provides for the mask to be secured at a mid or balance or pivot point for forces holding the mask in place and prevents movement of the mask off the face.

Aspect b) of the mask FIG. 2 is particularly advantageous when the wearer has a maximally open mouth with extended jaw as in yawning, because the angles of the straps and forces applied by them provide to maintain the mask securely attached to the wearer's face and the anatomical features thereof and thus maintains an effective primary barrier between wearer and environment. The mask effectively is held to a mid-point or pivotal point along its length. The fit to the nose and cheeks and under chin are noted as these are not revealed by the mask moving off the face either upwards or downwards as in the way of other face masks.

In a subsidiary aspect in accordance with the invention's broadest independent aspect, at least one embodiment of the mask is the straps being made of linear elastic rubberised material or similar non-allergenic material with non-adhesive skin-gripping properties to ensure even better security of the mask.

The mask is so designed that it is manufactured in one single process whereby the mask is cut and joined to the cut straps and joined ultrasonically. The mask is impregnated with the nanotechnology material in a second process but in a linear manufacturing train.

DETAILED DESCRIPTION OF THE FIGURES

Figure 1:
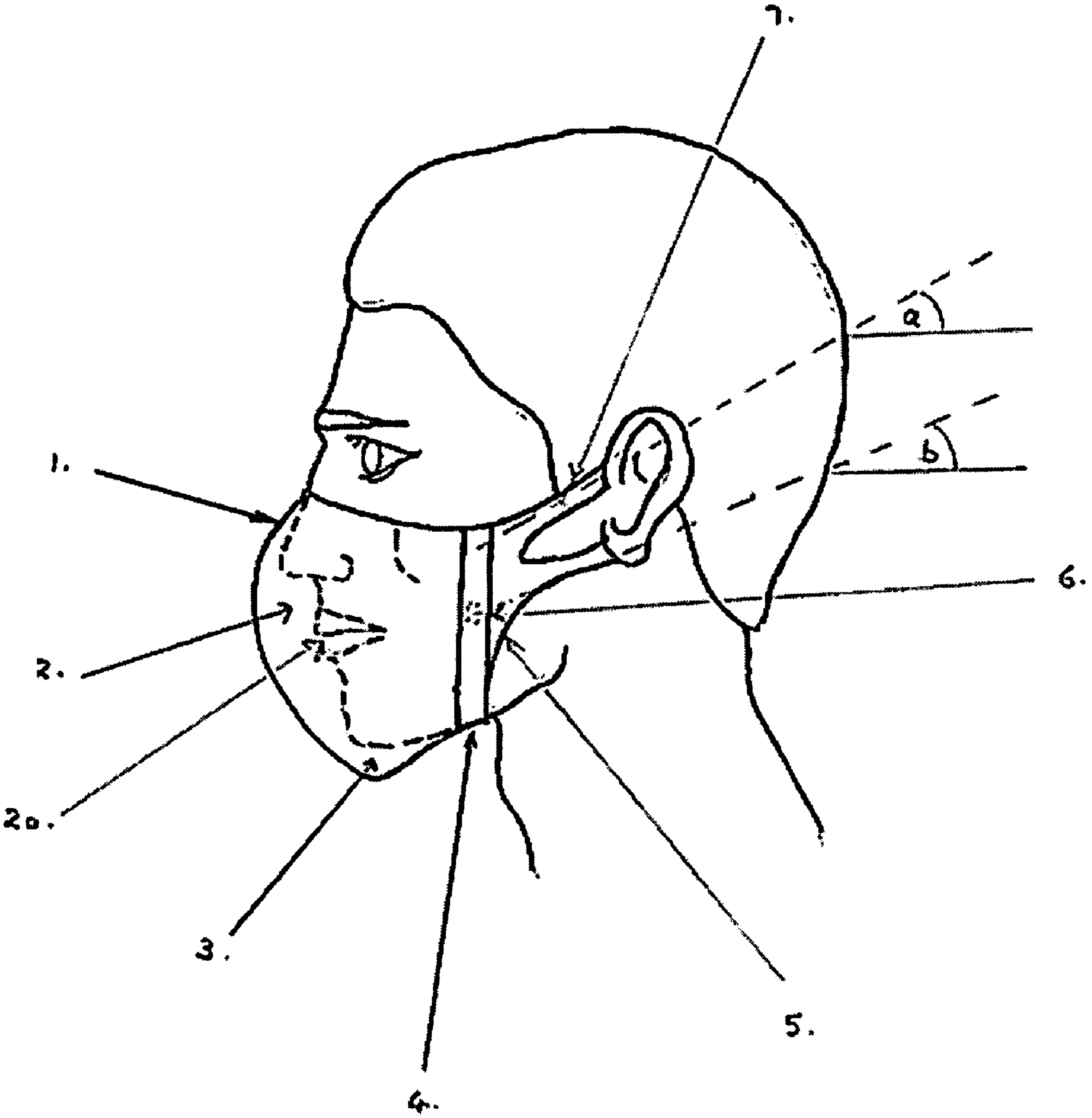
FIG. 1 Shows the side elevation of the mask in particular showing the fit to the facial features and the angles of the straps in the normal closed mouth position of the face.

FIG. 1. The diagram shows side elevation with the nose angle and space (1), the comfortable breathing space (2) created in front of the mouth (2*a*), chin recess and space (3), mask to straps seam is shown (4) and the mid point, balance point or pivotal point for the mask (6) is dotted in to explain the point of minimal movement of the mask. The lower strap (5) is attached to the mask at a point midway between the chin and pivot point while the upper strap (7) is attached at the upper part of the mask. Importantly the angle (a) of the upper strap is between 30 and 60 degrees and preferably 45 degrees depending upon the wearers face. Similarly angle (b) is between 10 and 40 degrees and preferably 25 degrees depending upon the wearers face.

Figure 2:
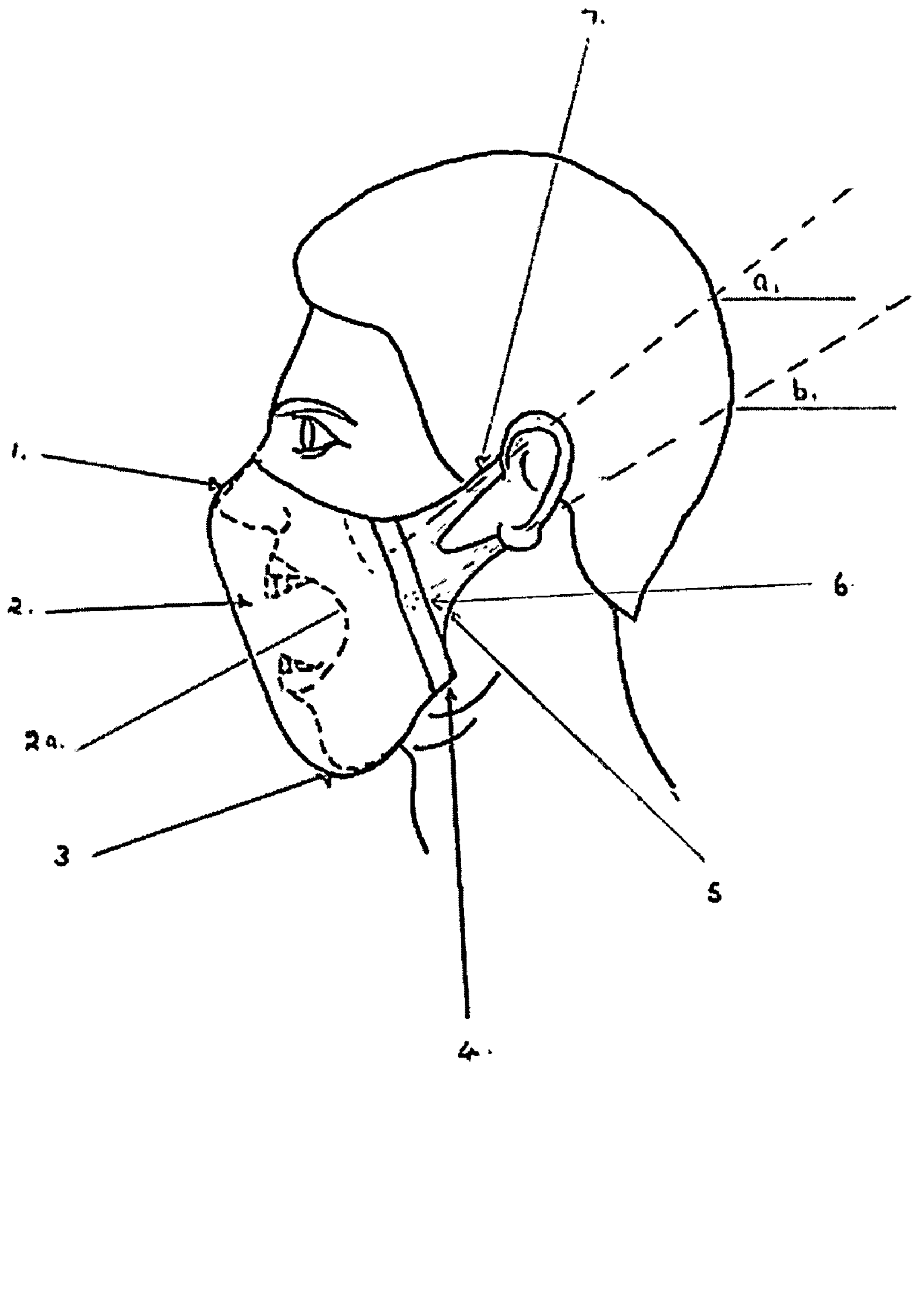
FIG. 2 Shows the same side elevation of the mask but in particular showing the face in a maximally open-mouth position with the jaw fully extended. The mask is tensioned by the facial movement but not disturbed from the face due to the positioning of the straps and the upper nose covering region and the chin space and chin (dotted in).

FIG. 2. Essentially similar diagram but importantly showing the upper strap angle (a1) to be between 40 and 70 degrees but preferably 50 degrees and created by the mouth being maximally opened (2*a*) and causing chin space (3) to be minimised. Similarly the lower strap angle (b1) is between 20 and 50 degrees and preferably 40 degrees caused by the open mouth and movement of the jaw. Nose space (1) is shown drawn close to the bridge of the nose by the facial movements.

LIST OF DESCRIPTION OF NUMERALS AND SYMBOLS FOR MAJOR ELEMENTS

1 nose angle and space
2 comfortable breathing space
2*a* mouth
3 chin recess and space
4 mask to straps seam
5 lower strap
6 mask
7 upper strap
a angle
a1 upper strap angle
b angle
b1 lower strap angle

What is claimed is:

1. A close-fitting face mask made of at least one of a woven or non-woven material, comprising:

a fitted nose area having a nose-bridge contact and a nose-bridge recess or space defined at an angle between 30° and 60° to the vertical;

a nose upper part adapted to extend from the nose-bridge contact at a mid-point of the bridge of a wearer's nose to the level of the wearer's lower eyelid;

a chin part having a chin recess or space adapted to extend 10 mm to 15 mm below the wearer's closed mouth chin level; and attachment straps made of elastic or flexible material stretchable to 25% to 50% of its length, including upper straps attached to the nose upper part and in the wearer's closed mouth position inclined at an angle of between 30° and 60° to the horizontal and adapted to pass above the upper part of the wearer's ear, and lower straps attached to a pivot or neutral point of the mask and inclined at an angle of 10° to 40° to the horizontal and adapted to pass below the wearer's ear, whereby forces are directed around the pivot or neutral point of the mask so that when the mask moves in response to the wearer's chin movement the mask subsequently returns to the original position established by the wearer when donning the mask.

2. A close-fitting face mask as claimed in claim 1 in which the mask material and optionally the ear strap material is impregnated with nanotechnology material that effects microbial killing of membrane-bound microorganisms and thus effectively prevents cross-contamination to the wearer or the environment, which includes other people.

3. A close-fitting face mask as claimed in claim 2 in which the nanotechnology material is of such a nature that it is bound to the mask material and optionally to the ear strap material and effects its microbial killing by mechanical action upon the membrane of membrane-bound microbes but is not harmful to humans and does not affect the normal flora of the skin of the wearer.

4. A close-fitting face mask as claimed in claim 1 such that it excludes particulate matter and allergens such as pollens spores and microbial particles and provides a barrier against the negative health effects of such particles such as in allergies, eczema and asthma.

5. A close-fitting face mask as claimed in claim 3 such that it excludes particulate matter and allergens such as pollens spores and microbial particles and provides a barrier against the negative health effects of such particles such as in allergies, eczema and asthma.

6. A close-fitting face mask as claimed in claim 1 wherein the nose-bridge recess is at 45° to the vertical.

7. A close-fitting face mask as claimed in claim 1 wherein the chin space is 12 mm in space but is adapted to fit underneath and at the sides of the wearer's chin.

8. A close-fitting face mask as claimed in claim 1 wherein said upper straps, in the wearer's closed-mouth position are inclined at an angle of 40° to the horizontal.

9. A close-fitting face mask as claimed in claim 1 wherein said lower straps are attached to the mid point of the mask at 25° to the horizontal.

* * * * *